United States Patent [19]
Waldstein

[11] 3,950,540
[45] Apr. 13, 1976

[54] AQUEOUS COMPOSITIONS CONTAINING TERTIARY AMINE OXIDES FOR TREATMENT OF RECTAL ITCHING AND LESSENING OF IRRITATION AND SWELLING OF PROLAPSED AND SWOLLEN EXTERNAL HEMORRHOIDS

[76] Inventor: David A. Waldstein, 622 Bergen Ave., Jersey City, N.J. 07304

[22] Filed: Nov. 1, 1973

[21] Appl. No.: 411,891

Related U.S. Application Data

[63] Continuation-in-part of Ser. No. 174,172, Aug. 23, 1971, abandoned, which is a continuation-in-part of Ser. No. 665,727, Sept. 6, 1967, abandoned.

[52] U.S. Cl. .............................................. 424/325
[51] Int. Cl.$^2$......................................... A61K 31/13
[58] Field of Search.......... 424/325; 260/583, 584 B

[56] References Cited
UNITED STATES PATENTS 3,202,714   8/1965   Zimmerer ......................... 260/584
3,296,145   1/1967   Findlan et al. ...................... 252/106

OTHER PUBLICATIONS

Grosicki et al. *Handbook of Non–Prescription Drugs* pp. 72–76 (1967).
Collins *Family Encyclopedia*, Ed. G. Sommerville, pp. 530–531 (1952).
Merck Index, 7 Ed. 1960, p. 421.

*Primary Examiner*—Leonard Schenkman
*Attorney, Agent, or Firm*—Kirschstein, Kirschstein, Ottinger & Frank

[57] ABSTRACT

Aqueous compositions containing compounds from the group consisting of bis polyalkoxy (C2-3) monoalkyl (C10-25) tertiary amine oxides and mono polyalkoxy (C2-3) dialkyl (C10-25) tertiary amine oxides, and a method of using such compositions for relieving rectal itching and lessening irritation and swelling of prolapsed and of irritated and swollen external hemorrhoids by topical application.

3 Claims, No Drawings

AQUEOUS COMPOSITIONS CONTAINING TERTIARY AMINE OXIDES FOR TREATMENT OF RECTAL ITCHING AND LESSENING OF IRRITATION AND SWELLING OF PROLAPSED AND SWOLLEN EXTERNAL HEMORRHOIDS

This application is a continuation-in-part of application Ser. No. 174,172, filed Aug. 23, 1971, which is a continuation-in-part of application Ser. No. 665,727, filed Sept. 6, 1967, both now abandoned.

BACKGROUND OF THE INVENTION

1. Field of the Invention

An aqueous composition containing a polyalkoxy alkyl tertiary amine oxide selected from the group consisting of bis polyalkoxy(C2-3) monoalkyl(C10-25) tertiary amine oxides and mono polyalkoxy (C2-3) dialkyl(C10-25) tertiary amine oxides, and a method of topically applying such a composition to a person's rectum for relieving itching and lessening irritation and swelling of external hemorrhoids.

2. Description of the Prior Art

Heretofore, rectal itching has been alleviated to some extent by laving and cleansing affected parts with water, and soap and water solutions with or without rectal irrigation. It also has been proposed to use various prescribed medicated suppositories and salves including, for example, cortisone, and to hypodermically inject prescribed medication into hemorrhoids. In addition, many proprietary remedies have been sold over-the-counter. However, none of the foregoing treatments and materials has proven to be fully acceptable because of failure to satisfactorily alleviate the symptoms or correct the cause or because of the inability of the sufferer to practice the suggested regime on himself.

SUMMARY OF THE INVENTION

Purposes of the Invention

It is an object of the invention to provide a novel aqueous composition including a compound selected from the group consisting of bis polyalkoxy(C2-3) monoalkyl(C10-25) tertiary amine oxides and mono polyalkoxy(C2-3) dialkyl(C2-25) tertiary amine oxides to be used for the alleviation of rectal itching and the lessening of irritation and swelling of external hemorrhoids.

It is another object of the invention to provide a method using such composition for relieving rectal itching and lessening irritation and swelling of prolapsed and of irritated and swollen external hemorrhoids.

Other objects of the invention in part will be obvious and in part will be pointed out hereinafter.

Brief Description of the Invention

The foregoing objects of the invention are obtained by the use in water of a polyalkoxy(C2-3) alkyl(C10-25) tertiary amine oxide from the group consisting of bis polyalkoxy(C2-3) monoalkyl(C10-25) tertiary amine oxides and mono polyalkoxy(C2-3) dialkyl(C10-25) tertiary amine oxides where the bis polyalkoxy(C2-3) monoalkyl(C10-25) tertiary amine oxides are of the formula

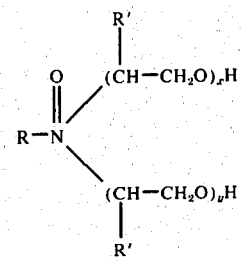

where R is a saturated or unsaturated fatty alkyl having from 10 to 25 carbon atoms, each R' is hydrogen or methyl, $x$ is at least 2, $y$ is at least 2, and $x + y$ is from 5 to 60, and where the mono polyalkoxy(C2-3) dialkyl(C10-25) tertiary amine oxides are of the formula $$\begin{array}{c} R \\ \diagdown \\ N-(CH-CH_2O)_x H \\ \diagup \| \\ R \quad O \end{array}$$

where R and R' are the same as above and $x$ is from 5 to 60. Such a composition containing a polyalkoxy(C2-3) alkyl(C10-25) tertiary amine oxide is particularly useful for topical application to a rectal area affected by itching or for obtaining symptomatic relief of irritation and swelling of prolapsed and of irritated and swollen external hemorrhoids, the topical application being by immersing the affected area in a water bath containing the compound.

DESCRIPTION OF THE PREFERRED EMBODIMENTS

The method of the invention is carried out by topically applying to an affected area a water solution containing a polyalkoxy(C2-3) alkyl(C10-25) tertiary amine oxide selected from the group consisting of bis polyalkoxy(C2-3) monoalkyl(C10-25) tertiary amine oxides and mono polyalkoxy(C2-3) dialkyl(C10-25) tertiary amine oxides where the bis polyalkoxy(C2-3) monoalkyl(C10-25) tertiary amine oxides are of the formula $$\begin{array}{c} R' \\ | \\ O \quad (CH-CH_2O)_x H \\ \| \diagup \\ R-N \\ \diagdown \\ (CH-CH_2O)_y H \\ | \\ R' \end{array}$$

where R is a saturated or unsaturated fatty alkyl having from 10 to 25 carbon atoms, each R' is hydrogen or methyl, $x$ is at least 2, $y$ is at least 2, and $x + y$ is from 5 to 60, and where the mono polyalkoxy(C2-3) dialkyl(C10-25) tertiary amine oxides are of the formula

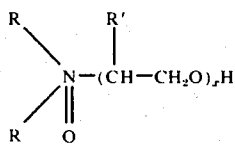

first series of reactions described is for the preparation of bis(polyethoxy) monoalkyl tertiary amine oxides.

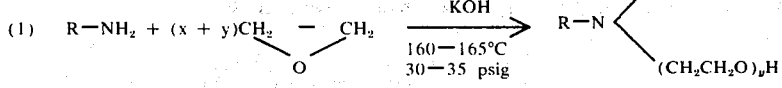

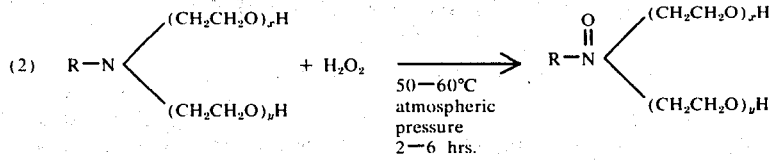

The second series of reactions is for the preparation of mono(polyethoxy) alkyl tertiary amine oxides wherein ethyleneoxide is used as the illustrative alkylene oxide reactant.

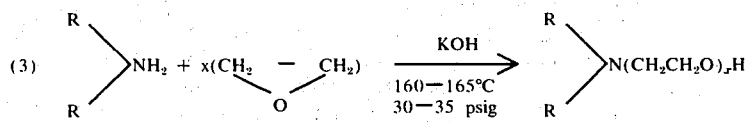

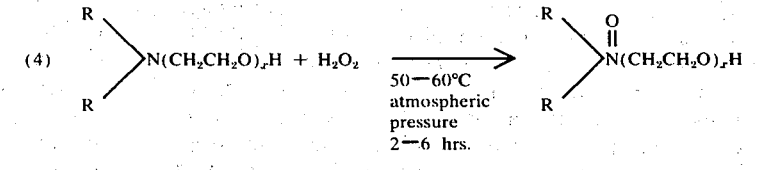

where R and R' are the same as above and $x$ is from 5 to 60.

The fatty alkyl group identified in the above formulae as R is a saturated alkyl such as palmityl, stearyl, myristyl, behenyl, coconut oil alkyls, and the like, as well as alkenyl such as oleyl, linoleyl, linolenyl, and the like. Preferably, said fatty alkyl group has from 12 to 22 carbon atoms.

The terms $x$ and $y$ indicate the values for the oxyethylene substituents. $x$ and $y$ each should range from 2 to 30 for the bis polyalkoxy(C2-3) monoalkyl(C10-25) tertiary amine oxides. The term $x + y$ indicates the cumulative value for the oxyethylene substituents and, as indicated above, is in the range of 5 to 60. In the preferred aspect of the invention the value of $x + y$ is from 5 to 45. In no event is the value of either $x + y$ less than 2 for the bis polyalkoxy(C2-3) monoalkyl(C10-25) tertiary amine oxide.

There must always be at least 5 oxyethylene substituents attached directly to the nitrogen atom for the mono polyalkoxy(C2-3) dialkyl(C10-25) tertiary amine oxides. $x$ as just indicated above ranges from 5 to 60 for the mono polyalkoxy(C2-3) dialkyl(C10-25) tertiary amine oxides.

The aforesaid polyalkoxy(C2-3) alkyl(C10-25) amine oxides useful in carrying out the invention can be prepared by the alkoxylation of a fatty alkyl amine and the oxidation of the resulting product according to the following reaction scheme wherein ethyleneoxide is used as the illustrative alkylene oxide reactant. The Reaction (1) is carried out by placing the alkyl amine, e.g. stearyl amine, in a closed reactor with an agitator under a pressure of two atmospheres in the presence of potassium hydroxide acting as a catalyst and maintaining the temperature between 160°C and 165°C. Ethyleneoxide is pumped in a steady flow into the reactor and the pressure gauge on the reactor is observed. The flow is maintained at a rate such that the pressure remains constant at two atmospheres, indicating that the desired absorption (reaction) of ethyleneoxide is taking place. The degree of polyethoxylation is determined by weighing the amount of ethyleneoxide introduced into the reactor. From 5 to 60 mols of ethyleneoxide will be absorbed in reaction (1) in from 2 to 6 hours. At the end of about 3 hours about 25 mols of ethyleneoxide are absorbed(reacted). Reaction (3) is carried out in exactly the same manner as reaction (1).

Reactions (2) and (4) are carried out at atmospheric pressure by mixing hydrogen peroxide with the compound formed by reaction (1) or (3) at atmospheric pressure for 4 to 5 hours. The following examples set forth in detail methods of preparing compounds representative of compounds of the present invention.

For the monoalkyl polyethoxy amine commercial hydrogenated tallow amine which consists principally of stearyl amine is reacted pursuant to reaction (1) with approximately 25 molar equivalents of ethyleneoxide in the presence of 0.2 to 0.4% by weight of potassium hydroxide based upon the weight of the hydrogenated tallow amine. The reaction is carried out for approximately 3 hours, the product being sampled from time to time to determine the degree of polyethoxylation, and once the time is known, the reaction being repeated for the same length of time and under the same reaction conditions. To 1360 grams of the bis(polyethoxylated) product secured from reaction (1) containing 25 mols of ethyleneoxide and which is maintained at a temperature of about 35°C there is added slowly with vigorous agitation 130 grams of 35% hydrogen peroxide. After mixing for two hours the temperature of the reaction mixture raises exothermically to about 60°C and the mixture is stirred for an additional two hours.

After being allowed to stand overnight at room temperature the reaction mixture is heated to about 70° to 80°C to remove all unreacted hydrogen peroxide and then cooled to room temperature.

The reaction product obtained is a bis(polyethoxy)-monotallow tertiary amine oxide containing approximately 25 molar equivalents of ethyleneoxide. The reaction product contains some water derived from the hydrogen peroxide, the amount of water being about 10–20% depending upon the degree of polyethoxylation and molecular weight of the tertiary amine. In compositions detailed hereinafter, this amount of water has been taken into account except where the term "reaction product" is employed, which term includes the water present in the reaction product.

To prepare a ditallow mono(polyethoxy) tertiary amine oxide the same procedure is followed as for preparing a monotallow bis(polyethoxy) tertiary amine oxide except that the starting amine is ditallow amine, the reaction time for preparing the ditallow polyethoxy tertiary amine taking approximately three hours to incorporate approximately 25 molar equivalents of ethylene oxide. The catalyst is the same. The amount of ditallow mono(polyethoxy) tertiary amine which is oxidized with hydrogen peroxide and the amount of hydrogen peroxide employed for oxidation is the same as that employed for the oxidation of the monotallow bis(polyethoxy) tertiary amine to a monotallow bis(polyethoxy) tertiary amine oxide.

The same process as outlined above is likewise employed to make a monolauryl bis(polyethoxy) tertiary amine oxide and a dilauryl mono(polyethoxy) tertiary amine oxide, the time for ethyoxylation to incorporate 25 molar equivalents of oxide being approximately three hours under the same conditions as mentioned above. However, in the oxidation step 1450 grams of the nonoxidized ethoxylated amine is reacted with 130 grams of 35% hydrogen peroxide.

To manufacture polyethoxy oleyl amines of the monooleyl and dioleyl and the bis(polyethoxy) and mono(polythoxy) tertiary amine oxide types, respectively, the same practice is again followed using 950 grams of the unoxidized polyethoxylated product with the same amount of hydrogen peroxide as set forth above.

If it is desired to have a lower molar equivalent of ethylene oxide the polyethoxylation step is carried out for a shorter period of time, e.g. for 15 mols of ethylene oxide in the neighborhood of 1½ hour. If a higher molar equivalent of ethylene oxide is desired to be incorporated the polyethoxylation step is carried out for a longer period of time, e.g. in the neighborhood of 4½ hr. for a 45 molar equivalent of ethylene oxide and 6 hrs. for incorporation of 60 molar equivalents of ethylene oxide.

For the monoalkyl polypropoxy [$CH_3CHCH_2O$] amine commercial hydrogenated tallow amine which consists principally of stearylamine is reacted pursuant to reaction (1) with approximately 25 molar equivalents of propyleneoxide in the presence of 0.2 to 0.4% by weight of potassium hydroxide based upon the weight of the hydrogenated tallow amine. The reaction is carried out for approximately 3 hours, the product being sampled from time to time to determine the degree of polypropoxylation, and once the time is known, the reaction being repeated for the same length of time and under the same reaction conditions. To 1470 grams of the bis(polypropoxylated) product secured from reaction (1) containing 25 mols of propyleneoxide and which is maintained at a temperature of about 35°C there is added slowly with vigorous agitation 130 grams of 35% hydrogen peroxide. After mixing for 2 hours the temperature of the reaction mixture raises exothermically to about 60°C and the mixture is stirred for an additional two hours.

After being allowed to stand overnight at room temperature the reaction mixture is heated to about 70° to 80° C to remove all unreacted hydrogen peroxide and then cooled to room temperature.

The reaction product obtained is a bis(polypropoxy) monotallow tertiary amine oxide containing approximately 25 molar equivalents of propyleneoxide.

The same reactions as set forth above employing only different alkyl groups and different amounts of the unoxidized polyalkoxylated amines in the oxidation step and different lengths of time for the alkoxylation step are used to produce the following polyalkoxy alkyl tertiary amine oxide reaction products all embodying the present invention and all useful for compositions and treatments pursuant to the present invention.

In all instances the degree of polyalkoxylation indicated for the bis(polyalkoxy) amines is approximately uniformly divided between the two polyalkoxy groups or reverting to the $x$ and $y$ terminology, $x$ is approximately equal to $y$.

monostearyl bis(polyethoxy)tertiary amine oxide (with 5, 15, 25, 45 or 60 mols ethyleneoxide);
monotallow bis(polyethoxy) tertiary amine oxide (with 5, 15, 25, 45 or 60 mols ethyleneoxide);
monolauryl bis(polyethoxy) tertiary amine oxide (with 5, 15, 25, 45 or 60 mols ethyleneoxide);
monococo bis(polyethoxy) tertiary amine oxide (with 5, 15, 25, 45 or 60 mols ethyleneoxide);
monomyristyl bis(polyethoxy) tertiary amine oxide (with 5, 15, 25, 45 or 60 mols ethyleneoxide);
monobehenyl bis(polyethoxy) tertiary amine oxide (with 5, 15, 25, 45 or 60 mols ethyleneoxide);
monopalmityl bis(polyethoxy) tertiary amine oxide (with 5, 15, 25, 45 or 60 mols ethyleneoxide);
monosoya bis(polyethoxy) tertiary amine oxide (with 5, 15, 25, 45, or 60 mols ethyleneoxide);
monooleyl bis(polyethoxy) tertiary amine oxide (with 5, 15, 25, 45 or 60 mols ethyleneoxide);
distearyl mono(polyethoxy) tertiary amine oxide (with 5, 15, 25, 45 or 60 mols ethyleneoxide);
ditallow mono(polyethoxy) tertiary amine oxide (with 5, 15, 25, 45 or 60 mols ethyleneoxide);
dilauryl mono(polyethoxy) tertiary amine oxide (with 5, 15, 25, 45 or 60 mols ethyleneoxide);
dicoco mono(polyethoxy) tertiary amine oxide (with 5, 15, 25, 45 or 60 mols ethyleneoxide);
dioleyl mono(polyethoxy) tertiary amine oxide (with 5, 15, 25, 45 or 60 mols ethyleneoxide);

monostearyl bis(polypropoxy) tertiary amine oxide
  (with 5, 15, 25, 45 or 60 mols propyleneoxide);
monotallow bis(polypropoxy) tertiary amine oxide
  (with 5, 15, 25, 45 or 60 mols propyleneoxide);
monolauryl bis(polypropoxy) tertiary amine oxide
  (with 5, 15, 25, 45 or 60 mols propyleneoxide);
monococo bis(polypropoxy) tertiary amine oxide
  (with 5, 15, 25, 45 or 60 mols propyleneoxide);
monomyristyl bis(polypropoxy) tertiary amine oxide
  (with 5, 15, 25, 45 or 60 mols propyleneoxide);
monobehenyl bis(polypropoxy) tertiary amine oxide
  (with 5, 15, 25, 45 or 60 mols propyleneoxide);
monopalmityl bis(polypropoxy) tertiary amine oxide
  (with 5, 15, 25, 45 or 60 mols propyleneoxide);
monosoya bis (polypropoxy) tertiary amine oxide
  (with 5, 15, 25, 45 or 60 mols propyleneoxide);
monooleyl bis(polypropoxy) tertiary amine oxide
  (with 5, 15, 25, 45 or 60 mols propyleneoxide);
distearyl mono(polypropoxy) tertiary amine oxide
  (with 5, 5, 25, 45 or 60 mols propyleneoxide);
ditallow mono(polypropoxy) tertiary amine oxide
  (with 5, 15, 25, 45 or 60 mols propyleneoxide);
dilauryl mono(polypropoxy) tertiary amine oxide
  (with 5, 5, 25, 45 or 60 mols propyleneoxide);
dicoco mono(polypropoxy) tertiary amine oxide
  (with 5, 15, 25, 45 or 60 mols(propyleneoxide);
dioleyl mono(polypropoxy) tertiary amine oxide
  (with 5, 15, 25, 45 or 60 mols propyleneoxide).

Commercial fatty alkyl amines are used in the production of compounds of the instant invention. As is well known, commercial tallow amine contains about 75% of stearyl and palmityl, and 25% of oleyl. A commercial soya amine contains about 52% of linoyl, 33% of oleyl, 7% of stearyl and palmityl and 8% of others, and a commercial coco contains about 40% lauryl, 15% myristyl, 15% oleyl and stearyl, and the balance hexyl, octyl and decyl.

There now will be pointed out manners in which polyalkoxy alkyl tertiary amine oxide reaction products such as described above can be used for the relief of rectal itching, and the lessening of irritation and swelling of prolapsed irritated and swollen hemorrhoids by topical application in a water solution to the affected areas.

The tertiary amine oxides of the invention are incorporated in water which is chemically inert to the tertiary amine oxides. The amount of the active ingredient, to wit, the tertiary amine oxides of the invention, can be varied very widely. For example, as little as 0.01% by weight of the tertiary amine oxide of the invention in a water solution will relieve symptoms of the character under consideration. The presence of larger percentages, up to 50%, enhances the relief or lessens the time of treatment. The preferred range is from 0.01 to 10% by weight in water.

In these proportions the composition is watery. It can be used as a sitz bath, i.e. placed in a shallow receptacle in which the afflicted patient sits with the affected areas exposed to the composition.

Another method using a water solution of the tertiary amine oxides of the invention is to provide a composition in the form of a concentrate, e.g. a 25% by weight water soluton of a tertiary amine oxide of the invention, and then to disperse one to two ounces of the concentrate in a bathtub full of water, e.g. about 14 gallons. With one ounce of such concentrate the concentration of the tertiary amine oxide is approximately 0.05% by weight and with 2 ounces about 0.1% by weight. It has been found that excellent results are obtained where the tertiary amine oxides of the invention are present in a bathtub full of water in a range of from about 0.01 to 0.5% by weight.

An excellent regime, either in a bathtub or in a sitz bath (this regime is merely exemplificative, inasmuch as any regime is acceptable where the affected parts have an amine of the invention applied thereto in any concentration from fully concentrated down to extreme dilutions, even as low as 0.01% by weight) is to immerse the affected part in a bathtub or sitz bath containing a water solution of a tertiary amine oxide of the invention in the dilution range mentioned above.

As a matter of general hygiene in any regime using a tertiary amine oxide of the invention, the patients are instructed to use cotton and warm water instead of toilet tissue after defecation. The patients bathe 1 to 3 times a day in a water bath containing a tertiary amine oxide of the invention, e.g. a bathtub or sitz bath of water in the concentration range indicated. It should be noted that the high end of the range is not advantageously exceeded, because at the high end good results are obtained which are not made noticeably better by increasing the concentration. The bathtub or the sitz bath is maintained at a temperature of about 110°F during immersion. Preferably, such a bath, either in a bathtub or in a sitz bath, is taken before retiring, and additional baths, if the severity of the affliction warrants, are taken once or twice during the day, e.g. once on arising, and once more at mid-day. The duration of the immersion is about 15 to 20 minutes. The longer the immersion, the better results. However, even short periods of immersion, e.g. 5 minutes, have been found to be useful. Noticeably good results usually are obtained in about 1 week, although if the condition is severe, longer periods of treatment are indicated, e.g. as much as 12 weeks.

In describing the water-based compositions containing the tertiary amine oxides of the invention over a wide range of percentages such as indicated, it is to be understood that good results are obtained with the complete spectrum of tertiary amine oxides listed above, and that the specific examples of weight proportions mentioned are applicable to each and every tertiary amine oxide, so that the following example of a use of the invention is only by way of illustration, and it is to be understood that the particular tertiary amine oxide mentioned in this example can be substituted by any one of the other tertiary amine oxides of the invention, and that symptomatic relief will be obtained with all of them.

EXAMPLE I

A concentrate is prepared by mixing 25% by weight of mono-tallow bis(polyethoxy, 15 mols ethylene oxide) tertiary amine oxide in water, i.e. 25 grams of said tertiary amine oxide and 75 cc of water. In making the computation of 25% by weight of the tertiary amine oxide, the amount of water in the reaction product has been taken into account. As noted above the same concentration will be useful if any other of the polyalkoxy alkyl tertiary amine oxides are employed. Any of these concentrates is added to a fourteen gallon bathtub of water and used for 10 to 15 minutes at the temperature above described.

EXAMPLE II

The above concentrate is added to one gallon of water to make a sitz bath which is used for 10 to 15 minutes at the temperature above described.

Another composition useful in the practice of the invention is the combination of a tertiary amine oxide of the invention and water wherein the amount of the tertiary amine oxide is from about 25 to about 40% by weight of the composition. Such a composition of the tertiary amine oxide with water is still somewhat watery and is employed in the practice of the invention by applying the same to affected areas with a cotton swab. The same hygienic regime as noted above with respect to immersion in a bathtub or in a sitz bath is followed with respect to rectal irrigation, topical rectal cleansing and frequency of and times of the day for application. Between the 10 figure and the 25% figure the mode of application can be either by immersion or by cotton swab.

At the higher concentrations (above 25%) the composition applied with a swab or by finger-smearing will tend to remain in the area because it has either an oily or creamy consistency. If it is desired to prevent staining of clothes and to prolong treatment, the composition after application may be protected with a gauze pad.

The time within which permanent relief from the mentioned symptoms is obtained, subject, of course, to fresh irritations which are not recurrences or reactivations of an old irritation, and when using any of the non-watery compositions, to wit, unguents and salves such as above described, ranges from about 1 to about 12 weeks depending upon the severity of the initial condition.

It is to be specifically observed that the compositions above recited are to be used for topical application in humans for the relief of rectal itching and lessening of irritation and swelling of prolapsed and of irritated and swollen external hemorrhoids.

Having described the invention there is claimed as new and desired to be secured by Letters Patent:

1. A method of treating external hemorrhoids in humans by relieving rectal itching and lessening of irritation and swelling of prolapsed and of irritated and swollen hemorrhoids, which method comprises immersing the affected area in a water bath containing as the active ingredient thereof from 0.01% to 0.5% by weight of a compound selected from the group consisting of

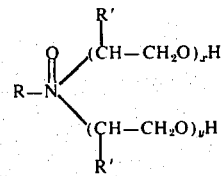

where R is a saturated or unsaturated fatty alkyl having from 10 to 25 carbon atoms, each R' is hydrogen or methyl, $x$ is at least 2, $y$ is at least 2, and $x + y$ are from 5 to 60, and

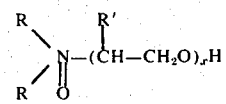

where R and R' are the same as above and $x$ is from 5 to 60.

2. A method as set forth in claim 1 wherein the immersion of the affected area is from about 5 to 20 minutes and is repeated daily for a period of from about 1 to 12 weeks.

3. A method as set forth in claim 1 wherein the compound is selected from the group consisting of monostearyl bis(polyethoxy) tertiary amine oxides, monotallow bis(polyethoxy) tertiary amine oxides, monolauryl bis(polyethoxy) tertiary amine oxides, monococo bis(polyethoxy) tertiary amine oxides, monomyristyl bis(polyethoxy) tertiary amine oxides, monobenyl bis(polyethoxy) tertiary amine oxides, monopalmityl bis(polyethoxy) tertiary amine oxides, monosoya bis(polyethoxy) tertiary amine oxides, monoleyl bis(polyethoxy) tertiary amine oxides, distearyl mono(polyethoxy) tertiary amine oxides, ditallow mono(polyethoxy) tertiary amine oxides, dilauryl mono(polyethoxy) tertiary amine oxides, dicoco mono(polyethoxy) tertiary amine oxides, dioleyl mono(polyethoxy) tertiary amine oxides, monostearyl bis(polypropoxy) tertiary amine oxides, monotallow bis(polypropoxy) tertiary amine oxides, monolauryl bis(polypropoxy) tertiary amine oxides, monococo bis(polypropoxy) tertiary amine oxides, monomyristyl bis(polypropoxy) tertiary amine oxides, monobehenyl bis(polypropoxy) tertiary amine oxides, monopalmityl bis(polypropoxy) tertiary amine oxides, monosoya bis(polypropoxy) tertiary amine oxides, monooleyl bis(polypropoxy) tertiary amine oxides, distearyl mono(polypropoxy) tertiary amine oxides, ditallow mono(polypropoxy) tertiary amine oxides, dilauryl mono(polypropoxy) tertiary amine oxides, dicoco mono(polypropoxy) tertiary amine oxides, and dioleyl mono(polypropoxy) tertiary amine oxides.

* * * * *